United States Patent
Tatman et al.

(10) Patent No.: US 12,233,414 B1
(45) Date of Patent: Feb. 25, 2025

(54) NON-HEALTHCARE SETTING BIOLOGICAL TESTING SYSTEM

(71) Applicant: Intrigue Health, Inc., San Diego, CA (US)

(72) Inventors: Dereck Tatman, San Diego, CA (US); Ron Mccullough, Encinitas, CA (US)

(73) Assignee: Intrigue Health, Inc., San Diego, CA (US)

( * ) Notice: Subject to any disclaimer, the term of this patent is extended or adjusted under 35 U.S.C. 154(b) by 0 days.

(21) Appl. No.: 18/288,967

(22) PCT Filed: Jul. 14, 2023

(86) PCT No.: PCT/US2023/027824
§ 371 (c)(1),
(2) Date: Oct. 30, 2023

(87) PCT Pub. No.: WO2024/025750
PCT Pub. Date: Feb. 1, 2024

Related U.S. Application Data

(60) Provisional application No. 63/393,203, filed on Jul. 28, 2022.

(51) Int. Cl.
*B01L 3/00* (2006.01)

(52) U.S. Cl.
CPC ... *B01L 3/502715* (2013.01); *B01L 3/502738* (2013.01); *B01L 3/50825* (2013.01); *B01L 2200/027* (2013.01); *B01L 2200/04* (2013.01); *B01L 2200/0647* (2013.01); *B01L 2200/0684* (2013.01); *B01L 2200/0689* (2013.01); *B01L 2300/023* (2013.01); *B01L 2300/042* (2013.01); *B01L 2300/0663* (2013.01); *B01L 2300/0681* (2013.01); *B01L 2400/0478* (2013.01); *B01L 2400/0605* (2013.01)

(58) Field of Classification Search
CPC ........ B01L 3/502715; B01L 3/502738; B01L 3/50825; B01L 2200/027; B01L 2200/04; B01L 2200/0647; B01L 2200/0684; B01L 2200/0689; B01L 2300/023; B01L 2300/042; B01L 2300/0663; B01L 2300/0681; B01L 2400/0478; B01L 2400/0605
USPC ...................................... 435/287.2
See application file for complete search history.

(56) References Cited

U.S. PATENT DOCUMENTS

| | | | |
|---|---|---|---|
| 8,506,908 B2 | 8/2013 | Benn | |
| 9,416,343 B2 | 8/2016 | Malik et al. | |
| 10,093,918 B2 | 10/2018 | Mielke et al. | |
| 2002/0046286 A1* | 4/2002 | Caldwell | G06F 16/27 709/229 |
| 2008/0149551 A1* | 6/2008 | Brugger | A61M 1/282 210/232 |
| 2009/0305337 A1* | 12/2009 | Iqbal | B01L 3/502715 435/286.2 |

(Continued)

*Primary Examiner* — Jill A Warden
*Assistant Examiner* — Jacqueline Brazin
(74) *Attorney, Agent, or Firm* — Manuel de la Cerra

(57) ABSTRACT

A non-healthcare setting kit for diagnosing a biological sample from a user is disclosed. The kit includes a mobile application that may run on a mobile device, a collection container for the biological sample, a cartridge that docks with the collection container and a reader that docks with the cartridge and that optically reads the biological sample.

36 Claims, 6 Drawing Sheets

(56) References Cited

U.S. PATENT DOCUMENTS

| | | | | |
|---|---|---|---|---|
| 2010/0291588 A1* | 11/2010 | McDevitt | ............. | G01N 33/491 |
| | | | | 435/287.1 |
| 2014/0127796 A1* | 5/2014 | Malik | ............... | B01L 3/502715 |
| | | | | 435/289.1 |
| 2015/0353919 A1* | 12/2015 | Mielke | ................. | B01L 3/5029 |
| | | | | 435/6.12 |
| 2019/0086380 A1* | 3/2019 | Harding | ............. | G01N 21/8483 |
| 2021/0308673 A1* | 10/2021 | Chiu | ................ | G01N 33/54386 |

* cited by examiner (Container Alignment)

(Container Docking)

NON-HEALTHCARE SETTING BIOLOGICAL TESTING SYSTEM

PRIORITY APPLICATIONS

This application is the Section 371 national filing of PCT Application PCT/US23/27824 titled "NON-HEALTHCARE SETTING BIOLOGICAL TESTING SYSTEM" filed on Jul. 17, 2023, which in turn claims priority to U.S. Provisional Application Ser. No. 63/393,203 titled "IN-HOME BIOLOGICAL TESTING SYSTEM" and filed on Jul. 28, 2022, and the entire contents of these applications are incorporated herein by reference in their entireties.

FIELD OF THE INVENTION

This invention relates to testing of biological samples.

BACKGROUND

Testing of biological samples has traditionally been situated in health care facilities or laboratories, which limits access to this testing for consumers, as they need to travel to appointments for testing, then wait for hours or days for the result to return. As ~70% of healthcare decisions are based on diagnostic testing, the historical standard leads to poor outcomes, disenfranchised patients and highly inefficient practice of care. The invention described herein has been designed to address this inefficiency by bringing clinical laboratory-quality testing directly into the home and to non-healthcare facilities. This invention will enable consumers to move from symptom to treatment within hours from the convenience of where they are, which will lead to better health outcomes and much happier consumers.

BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. Furthermore, various features of different disclosed embodiments can be combined to form additional embodiments, which are part of this disclosure. It will be understood that certain components and details may not appear in the figures to assist in more clearly describing the invention.

SUMMARY OF THE INVENTION

Figure 1:
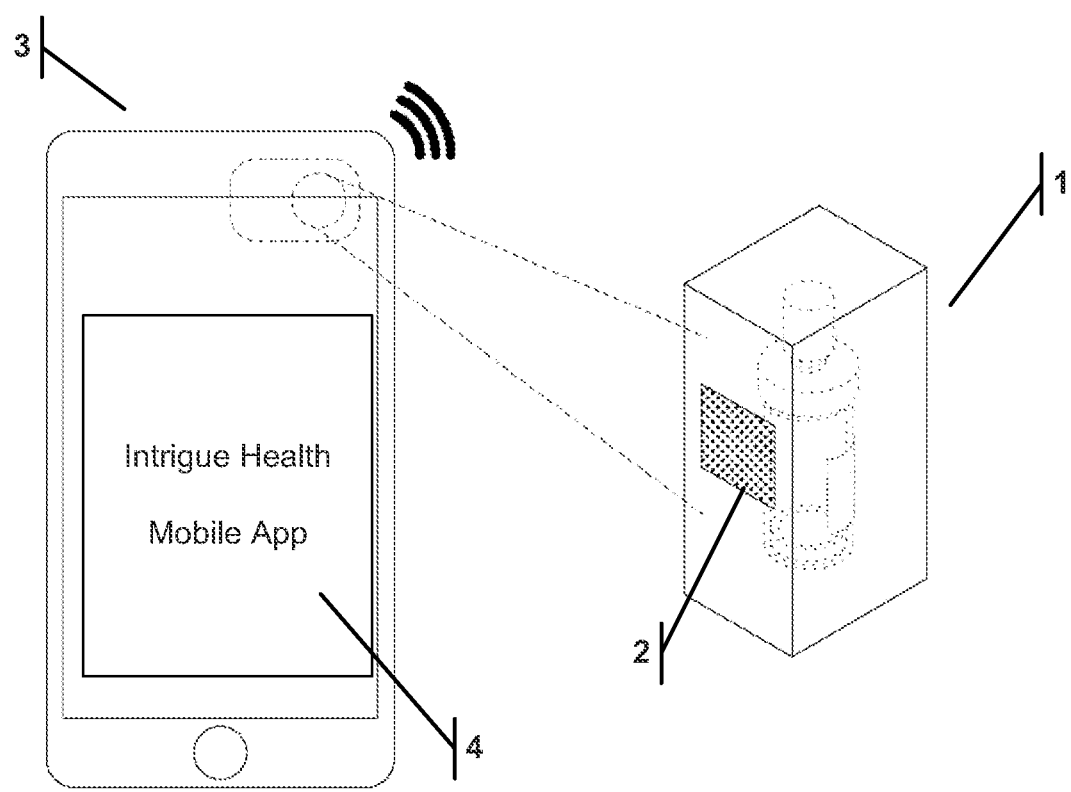
FIG. 1 illustrates scanning the product bar code into the mobile application.

A non-healthcare setting kit for diagnosing a biological sample from a user is disclosed. The kit includes a mobile application that may run on a mobile device, a collection container for the biological sample, a cartridge that docks with the collection container and a reader that docks with the cartridge and optically reads the biological sample. The collection container may have a cap that mounts onto the collection tube, and the cap includes a cap outlet. The cartridge may include a container port constructed to dock with the collection container, a reaction chamber with a first optical window that allows light to pass there through, and a microfluidic channel fluidly connecting the container port to the reaction chamber. The reader includes a light source that directs light through the first optical window of the reaction chamber, a sample injection piston that engages the collection container, a light detector that detects the light within the reaction chamber, a transmitter, a processor connected to the light source, the sample injection piston, the light detector, and the transmitter. The processor performs the following steps when the collection container is docked with the container port, and the reader is attached to the cartridge: (A) actuate the sample injection piston to force the biological sample from the collection container, through the cap outlet, the container port, the microfluidic channel and to the reaction chamber; (B) actuate the light source; and (C) receive data from the light detector.

The reaction chamber may include a composition that (1) interacts with a target in the biological sample when the target is present, and (2) changes a spectral characteristic of the light directed into the reaction chamber when there is an interaction. The target may be a small molecule, protein, DNA, RNA, a virus or a bacterium.

The light source may be an LED array or a laser. The light detector may be a photodiode array, a CCD sensor or a CMOS sensor.

The microfluidic channel may have one or more check valves and a filter.

The collection container may also include a buffer to preserve the biological sample. For example, the cap may include the buffer, and the buffer is released into the biological sample when the cap is mounted onto the collection tube.

The cartridge may include an extraction buffer reservoir fluidly connected to the reaction chamber. The reservoir may have a piston actuated by the processor to force the extraction buffer into the reaction chamber. The cartridge may also have a waste chamber, optionally having a vent, fluidly connected to the container port.

A valve may be used in the cartridge to regulate the flow of the biological sample between the container port and the reaction chamber. The reader may have a valve controller connected to the processor that controls the valve. A magnetic field may be used to control the valve.

Heating elements connected to the processor may be used to heat the collection container and the reaction chamber. When the cartridge contains multiple reaction chambers, the healing elements may be able to heat the reaction chambers to different temperature.

The reader may have a status indicator, a temperature sensor and a humidity sensor.

Additional aspects, alternatives, and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

DETAILED DESCRIPTION

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with the attached figures and is provided for ease of reference, where like reference numerals designate corresponding features throughout the specification and figures:

1 Non-healthcare Setting Testing Product
2 Barcode, QR code or RFID
3 Mobile Device
4 Mobile Application
5 Collection Container
10 Cap Lock
15 Cap
16 Cap Outlet
20 Collection Tube
22 Tube Bottom
23 Tube Volume
25 User
30 Biological Sample
35 Buffer Injection
40 Cartridge
45 Container Port
50 Extraction Buffer Reservoir
52 Reservoir Volume
54 Movable Wall
55 Check Valve
60 Biomarker Sorbent/Beads
65 Control Valve
70 Waste Microfluidic Channel
75 Reaction Chamber Microfluidic Channel
80 Reaction Chambers
82 Optical Window ((First)
83 Optical Window (Second)
85 Vent
90 Waste Chamber
95 Vent
100 Reader
110 Door
112 Cartridge Slot
115 Latch
120 Biological Sample Piston
125 Light Source
130 Light Detector
140 Heating Element (Reaction Chamber)
145 Interleaved Heating Element (Reaction Chamber)
150 Clamp
155 Clamp Constriction Movement
160 Heating Element (Door)
165 Buffer Pistons
170 Magnetic Valve Control
175 Processor
180 Temperature/Humidity Sensor
182 Status Indicator
185 Transceiver
190 Antenna
195 Remote Health Provider
200 Cloud Storage
205 Internet The system is comprised of three components that work together with the user mobile device to provide accurate, inexpensive and rapid test results. The three components are the collection container (illustrated in more detail in FIGS. 2A and 2B), the cartridge (illustrated in more detail in FIGS. 3A and 3B) and the reader (illustrated in more detail in FIGS. 4-5).

6.1 Collection Container

Figure 2C:
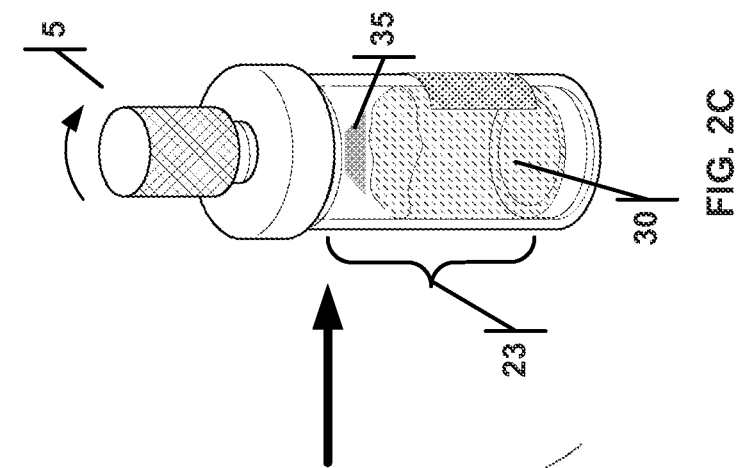
FIG. 2C illustrates the collection container with a biological sample.
Figure 2B:
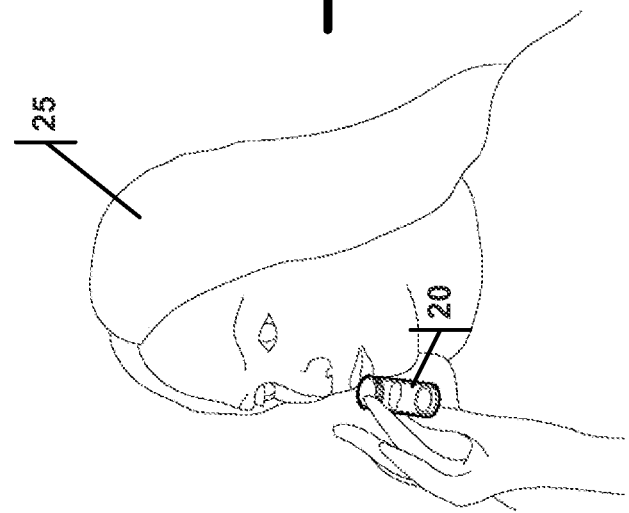
FIG. 2B illustrates the user depositing a biological sample into the collection container.
Figure 2A:
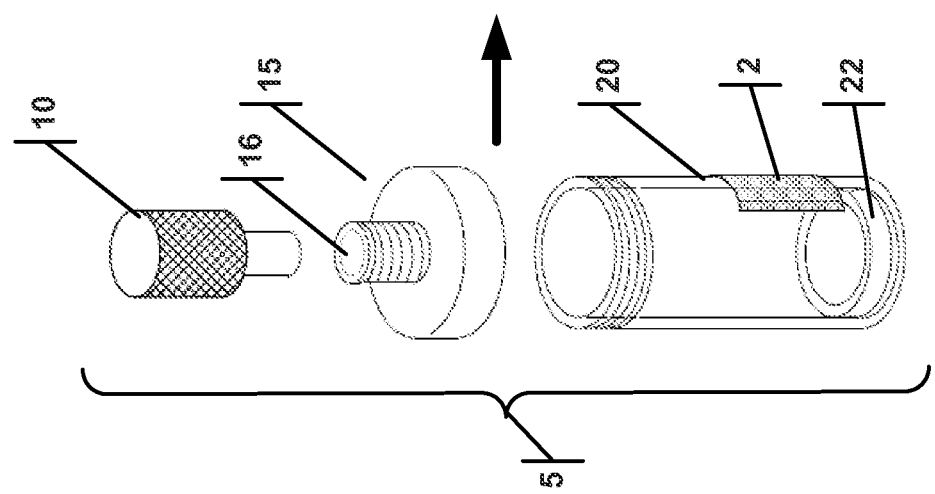
FIG. 2A is an exploded view of the collection container

FIG. 2A illustrates the collection container 5 comprised of a cap lock 10, a cap 15 with a cap outlet 16 and a collection tube 20. The user 25 deposits a biological sample 30 into the collection tube 20 (FIG. 2B). The collection container 5 preferably has a buffer solution loaded into it and is used as a tube for sample introduction (saliva, swab, urine, blood, etc.) into the reaction chamber of the cartridge (see FIGS. 3A and 3B). The buffer may be added either manually or, in a preferred manner, the cap 15 may have a buffer reservoir 18 that is released as a buffer injection 35 into the biological sample 30 once the cap 15 is screwed on the collection tube 20, as shown in FIG. 2C. A non-limiting example would include a blister pack that breaks when the cap 15 is mounted onto the collection tube 20, releasing the buffer.

The collection tube 20 has a tube bottom 22 with a gasket that acts as a plunger once inserted into the reader and a cap 15 that is applied after collection and locks into the cartridge via a Luer Lock connection or a similar connection. This locked junction serves as an injection point for the biological sample 30 into the microfluidic channels of the cartridge.

The mounted cap 15 and collection tube 2 define a tube volume 23 that holds the biological sample. By only having to deposit the biological sample 30 into the collection container 5, and thereafter not having to handle or expose the biological sample 30 again when introducing it into the cartridge or reader, the system is uniquely designed for easy non-healthcare setting use, including in-home use without suffering from possible testing errors arising from contamination or user error.

6.2 Cartridge

Figure 3A:
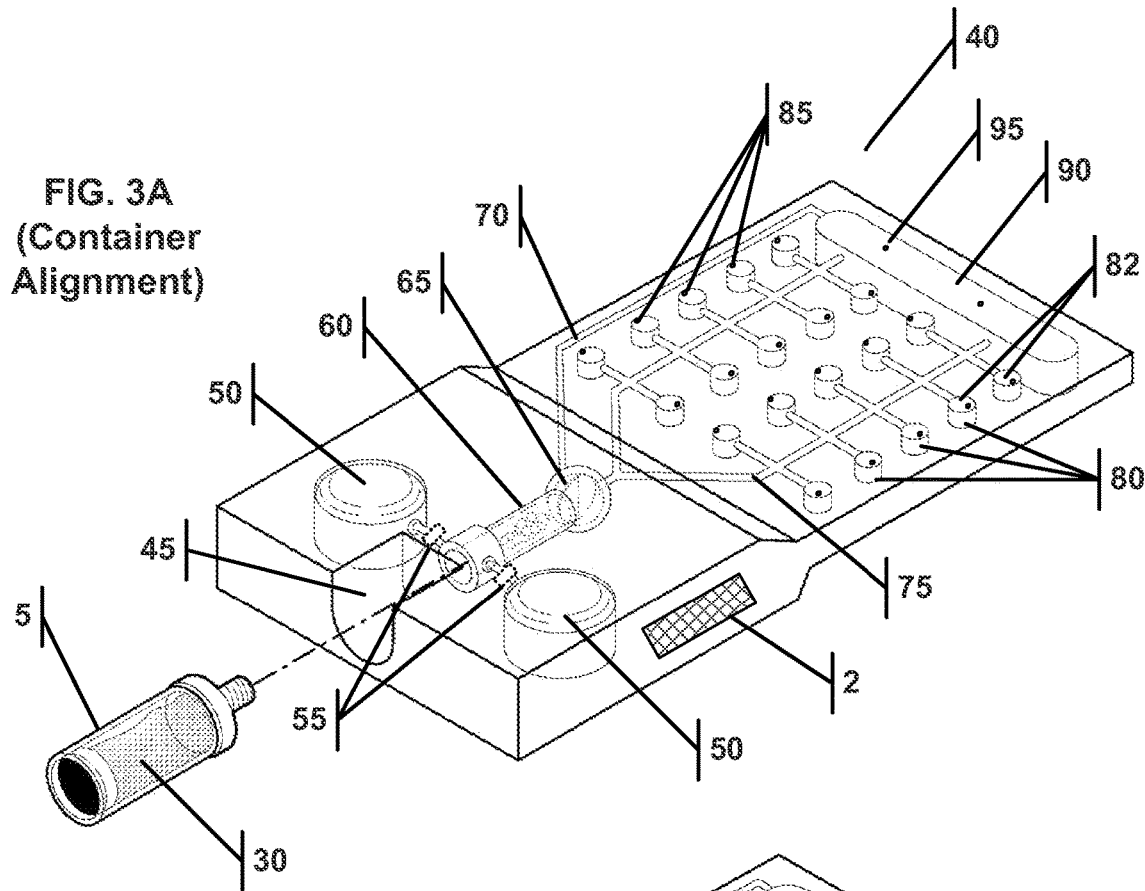
FIG. 3A illustrates the collection container aligned with the container port on a cartridge.
Figure 3B:
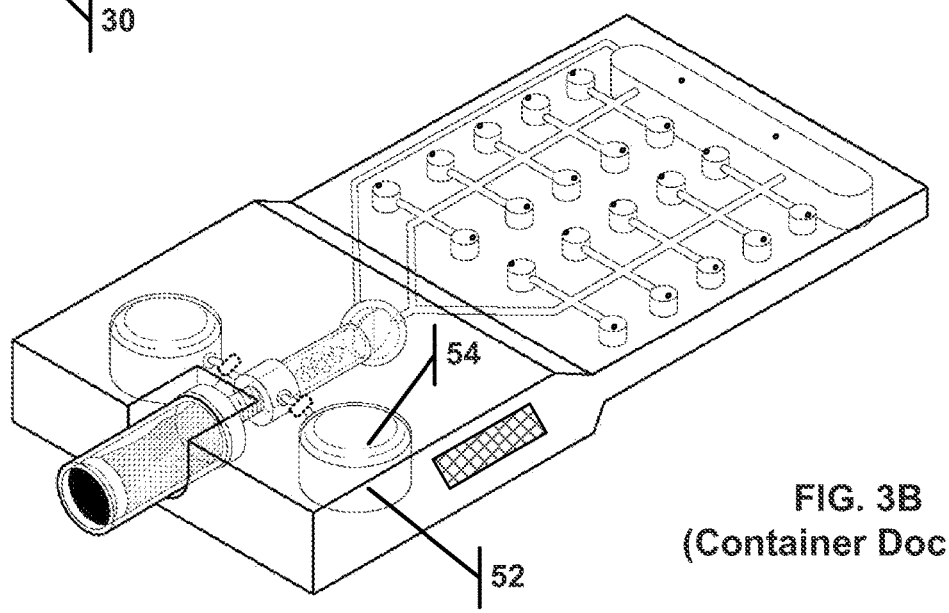
FIG. 3B illustrates the collection container docked in the container port of the cartridge.

FIG. 3A illustrates the collection container 5 with the biological sample 30 aligned with the container port 45 on a cartridge 40. In FIG. 3B the collection container 5 is docked and ready to introduce the biological sample 30 into the cartridge 40.

The cartridge 40 is a single-use injection-molded plastic, precision-laminated, silicon- or silica-containing chip that is housed, in part, within a plastic shell, with a container port 45 on one end, Its overall size is approximately 3 in×2 in×0.5 in. The cartridge 40 may contain microfluidic channels (70, 75), buffer reservoirs 50, a waste chamber 90, a sample filter 60, multiple reaction chambers 80 with optical windows 82 that allow light to pass through the reaction chamber, and magnetically controlled valves 65. The analytes and buffers will be modified to address the panel that is being tested. Each chamber 80 in the cartridge 40 can be prepopulated with a single assay or multiplexed biomarker assays that utilize optical detection. The assay may be a composition that (1) interacts with a target in the biological sample when the target is present, and (2) changes a spectral characteristic of the light directed into the reaction chamber when there is an interaction. In multiplexing, different reaction chambers may have different targets, allowing for multiple tests on one cartridge and from one biological sample. The target may be, but is not limited to, small molecules (e.g. drug metabolites, drugs, metals, etc.), proteins, DNA, RNA, viruses or a bacterium. The cartridge 40 contains a unique barcode 2, which will be scanned by the user app and will be the basis for beginning the analysis.

Broadly the cartridge 40 is capable of extracting target biomarkers from a variety of biological sample types because the extraction buffer reservoirs 50 can be manufactured to contain multiple lysis/elution buffers and can be incubated at a variety of temperatures from ambient up to 95 C for a multitude of optimized time periods. This incubation can be precisely controlled by the reader and its associated heating elements, as discussed below. The cartridge 40 can also be optimized for multiple biological sample types including saliva, urine, blood, or other biological samples. The reaction chambers 80 can be optimized and preloaded with various biomarker assays including isothermal and PCR molecular amplification assays, ELISA assays, as well as any other biochemical test that utilizes optical wavelengths as a biomarker detector. In addition, because the reader has broad-spectrum LED optics, each reaction chamber 80 can be multiplexed with different reporter fluorophores or colorimetric assays. Lasers may be used instead of or in combination with the LED array. The reaction chambers 80 can also be analyzed multiple times during the course of the reaction, and, when combined with targets of known quantities or an established standard curve, the assay can be both qualitative and quantitative.

The path of the biological sample 30 through the cartridge 40 will explain various subcomponents of the cartridge 40. The biological sample 30 exits the collection container through the cap outlet 16 and enters the cartridge 20 at the container port 45, and theextraction buffer reservoirs 50 are constructed to inject a buffer into the biological sample 30. The extraction buffer reservoir 50 define a reservoir volume 52 and a movable wall 54 that varies the reservoirs volume 52. As described in more detail below, the reader may have pistons that place pressure on the extraction buffer reservoirs 50 (i.e. on the movable wall 54), thereby precisely controlling the amount of buffer mixed into the biological sample 30. Check valves 55 prevent the biological sample 30 from entering the reservoirs 50. The biological sample 30 may then be filtered through biomarker sorbent/beads 60 and may travel to the magnetic control valve 65 that will precisely control the quantity of the biological sample to be introduced into the reaction chambers 80, via the reaction chamber microfluidic channels 75.

The reaction chambers may have transparent optical windows on the top 82 (first optical window) and bottom 83 (second optical window) of the cartridge 40 such that the light emitted from the light source 125 of the reader 100 may enter the reaction chamber 80 via the second optical window 83 and may exit the first optical window 82 to be detected by the photodiodes 130. The portion of the biological sample 30 that is not directed into the reaction chambers 80, may travel via the waste microfluidic channel 70 to the waste chamber 90. The reaction chamber 80 and waste chamber 90 may have vents (85, 95) to allow the flow of the biological sample 30 through the cartridge 40.

6.3 Reader

Figure 4:
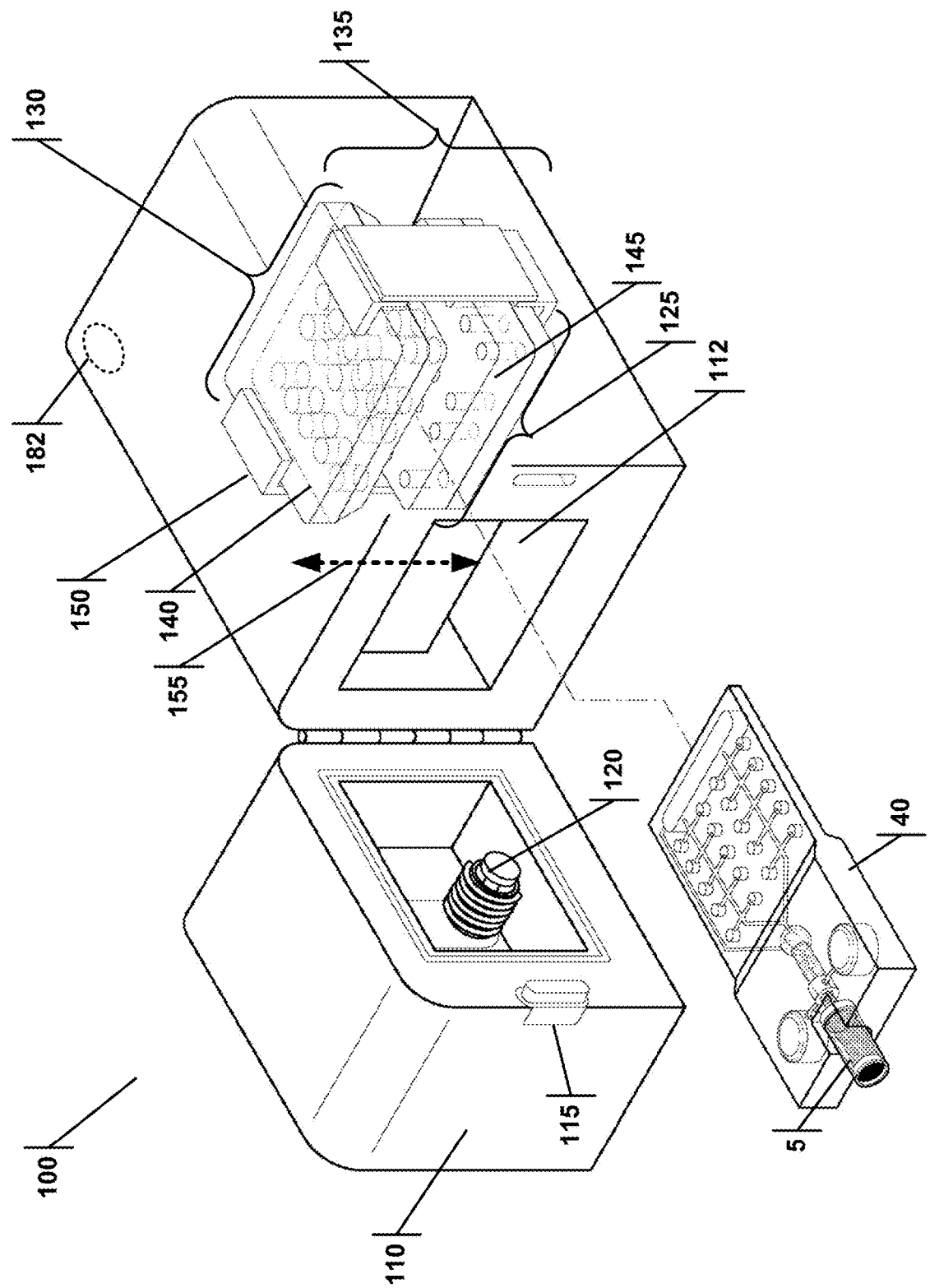
FIG. 4 is a cutaway view of the reader with certain components highlighted, as well as the insertion path of the cartridge (with the docked collection container) into the reader.
Figure 5:
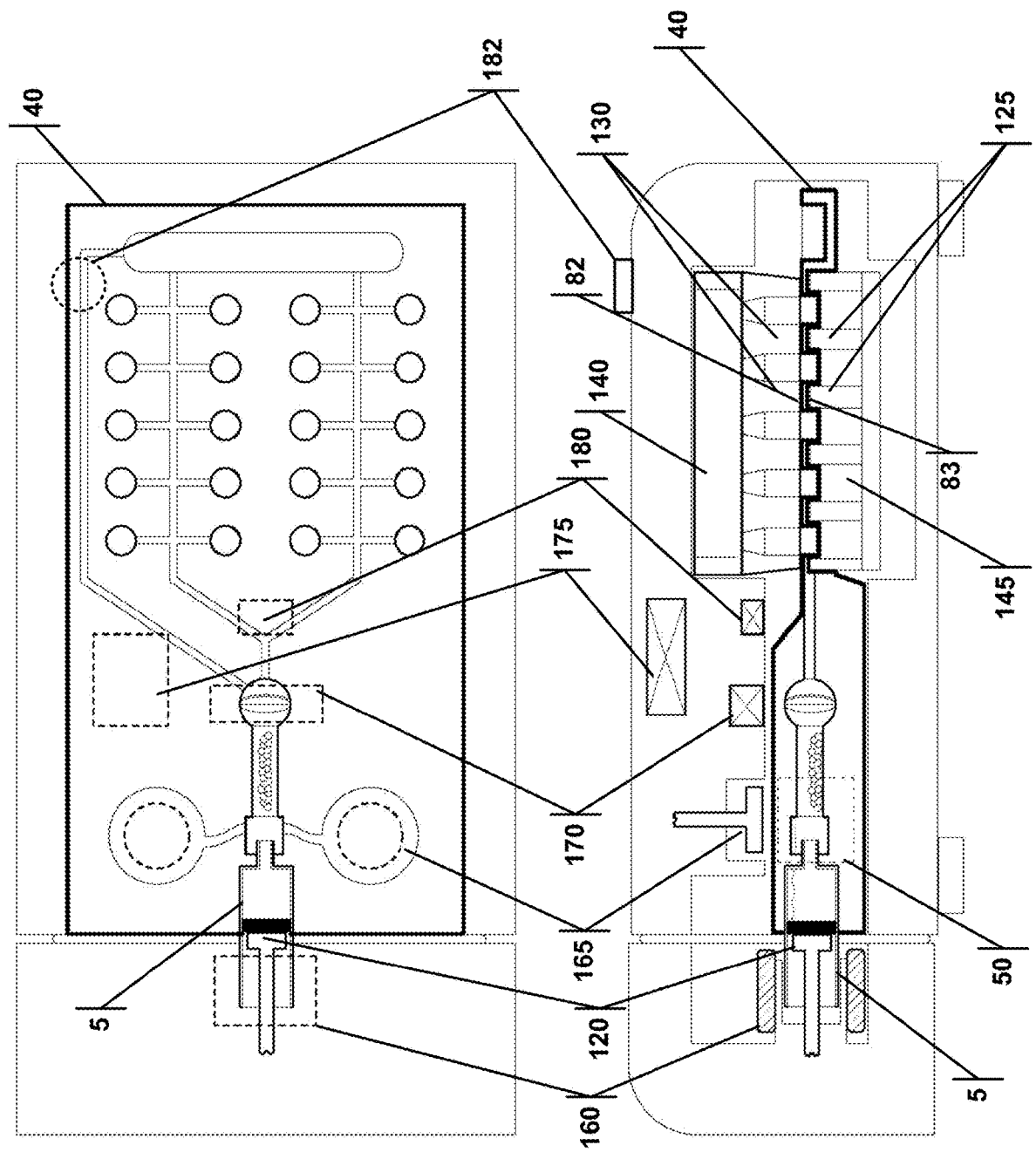
FIG. 5A is a top cross-section view of the reader with the cartridge/collection container inserted therein, illustrating various components of the system.
FIG. 5B is a side cross-section view of the reader with the cartridge/collection container inserted therein, illustrating various components of the system.
Figure 6:
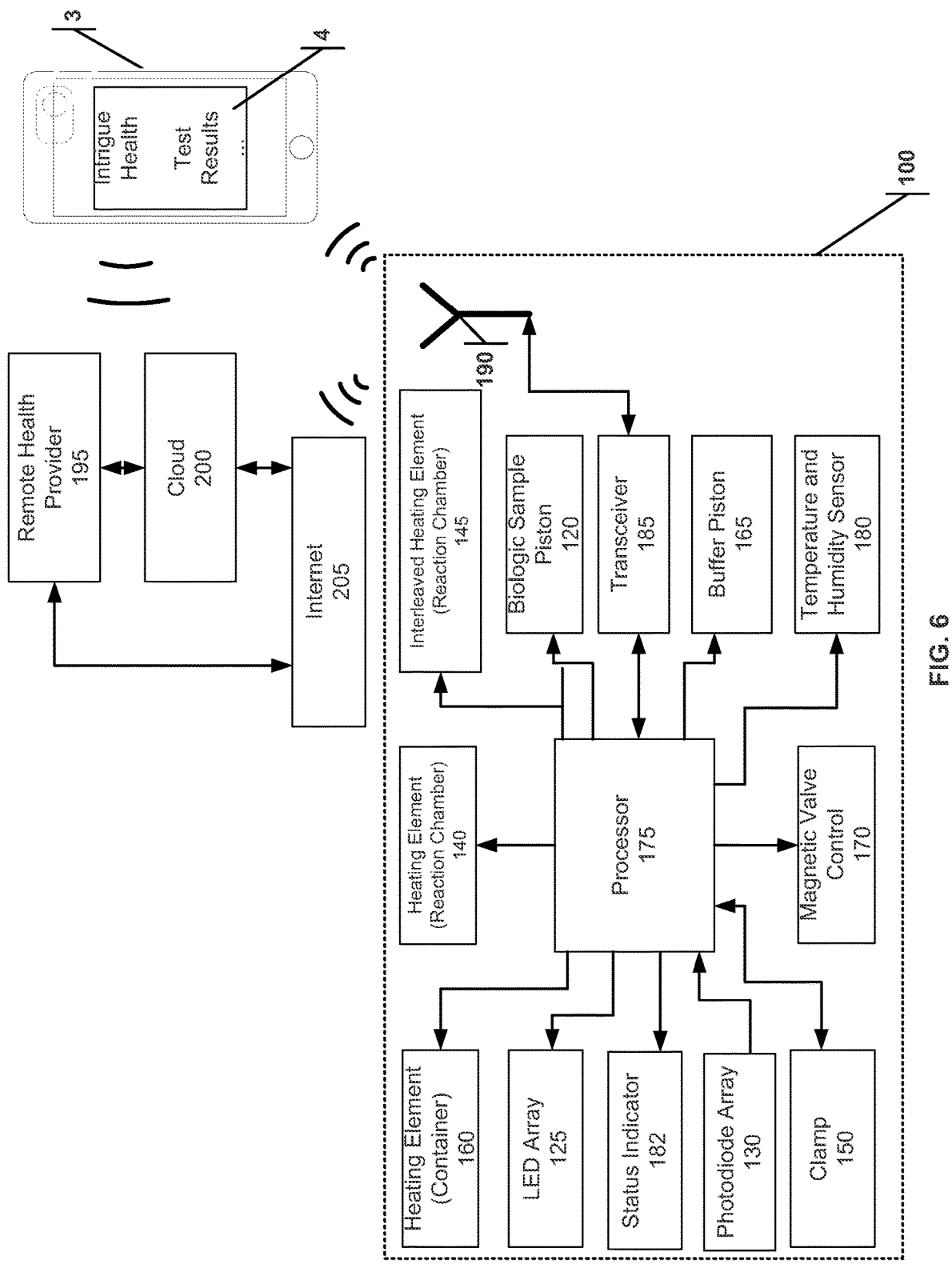
FIG. 6 is a diagram showing the connections to the processor and the data flow to the mobile device, remote health provider, the cloud and the Internet.

Referring to FIGS. 4 through 6, the reader 100 is a detection device that entirely encapsulates a fully loaded cartridge 40. The reader 100 can be powered via battery or wall outlet and contains a Bluetooth and a Wi-Fi enabled processor 175, a biological sample piston 120, magnetic valve control 170, temperature/humidity sensors 180, heating elements (140, 145, 160), a light source 125, a light detector 130 and buffer pistons 165.

The reader 100, through its processor 175, controls the assay-specific conditions, including reaction temperatures, time of reaction, movement of the biological sample, and detection parameters including detection frequency, emission wavelengths and detection wavelengths. Specifically, the pressure to migrate the biological sample 30 through the cartridge 40 is provided by a biological sample piston 120 located in the door 110 of the reader 100. The biological sample piston 120 is controlled by the software running on a processor 175. Directional fluidic movement, as well as extraction and wash steps, are achieved by the magnetic valve 65 in the cartridge 40, which are operated by the magnetic valve control 170, also controlled by the software running on a processor 175. The processor 175 also precisely controls reaction temperatures and humidity through the container heating element 160, the reaction chamber heating elements (140, 145), and the temperature/humidity sensor 180. The heating elements (140, 145) may have zones such that certain reaction chambers can be maintained at one temperature, while other reaction chambers are maintain at a different temperature. This accommodates various reactions that may have different optimal performance temperatures. This may be particularly advantageous when the system is used to multiplex (discussed more below).

The heating elements (140, 145, 160) may be, but are not limited to Peltier heater plates. The light source 125 may have cut outs that encircle the reaction chambers 80, and interleaved heating elements 145 may be interleaved into these cutouts to provide effective and controlled heating. Heating element 140 may be a plate that precisely heats the top side of the reaction chamber 80. The reason for these two heating elements (140, 145) is that during low-volume testing the biological sample 30 may condense on the top of the reaction chamber 80, and the heating element 140 will keep that from happening.

Two additional buffer pistons 165 are also controlled by the processor 175, and apply pressure to wash reagents and buffers in the extraction buffer reservoir(s) 50 on the cartridge 40. A light source directs light, preferably at multiple frequencies, through the reaction chambers 80 of the cartridge, which can then be detected by the light detector 130. The light detector may be a photodiode array, a CCD sensor or a CMOS sensor. As show in in FIGS. 5A and 5B, the light source 125 may be on the opposite side of the cartridge 40 as the light detector 130. In another embodiment, both the light source 125 and the light detector 130 may be on the same side of the cartridge 40. The control of the light source 125, and the data signal acquisition from the light detector 130, are accomplished by the processor 175. A status indicator 182 may be used to provide the user with visual and/or audio cues on the operation of the reader 100. The processor 175 may be connected to a transceiver 185 and antennae 190 to transmit data to a mobile application 4 operated on a mobile device 3. Data analysis may be performed exclusively by the mobile application 4 or may be shared with the processor 175, or exclusively by the processor 175. The processor 175 may store data and analysis results until connected to the mobile application 4 or to the Internet 205. Offloading all or much of the data analysis to the mobile application 4 allows for a much less expensive processor 175, reducing the reader 100 manufacturing costs. The mobile application 4 may also transfer data to a remote health provider 195, such as a hospital or doctor's office. FIG. 6 illustrates the various components connected to the processor 175 of the reader 100. Through the transceiver 185, the reader 100 can communicate with the mobile application 4. Optionally, the mobile application 4 can also communicate with a remote health provider 195 and can also communicate wih the Cloud 200.

The reader 100 connects to the mobile application 4 via Bluetooth, and will receive firmware or software upgrades through the mobile application 4. The reader 100 may also connect to the Internet 205 directly via WIFI or other wireless protocol to receive firmware or software upgrades, and also to transmit test data to the Cloud 200 or to the remote health provider 195.

The light source 125, the light detector 130, and the heating elements (140, 145) may be part of a clamp 150 that constricts (see movement 155) the cartridge 40 during operation. This constriction may be accomplished through, but is not limited to, a spring-loaded mechanism that squeezes onto the cartridge when the door is closed, or a electro mechanical device actuated by the processor 175 when in operation. This constriction provides a physical barrier to prevent light leakage between reaction chambers 80 and also provides a thermal barrier between the individual reaction chambers 80.

Mechanically, the reader 100 ensures the alignment of the light source 125 and the light detector 130 with the optical windows on the cartridge 40 and, after the door 110 is closed and the latch 115 actuated, the biological sample piston 120 (controlled by the processor 175) provides the kinetic force to migrate the biological sample 30 through the cartridge 40. The consolidation of all mechanical components on the reader 100 greatly reduces the cost and complexity of manufacture.

6.4 Method for Using System

Now a method of using the system will be detailed. The user logs into the mobile application 4 and scans or enters the barcode 2 for the test kit (FIG. 1). The barcode 2 may instead be a QR code or RFID tag. The user 25 then indicates who will be tested and is asked a series of symptom related questions to ensure the cartridge is appropriate for testing. A biological sample 30 such as saliva, urine, blood or other biological sample is collected and placed in a collection tube 20. (FIG. 2B). The cap 15 is locked on to the collection tube 20, releasing the buffer injection 35 into the biological sample (FIG. 2C). The collection container 5 is then aligned and docked onto the cartridge 40. (FIGS. 3A and 3B). The cartridge 40 is inserted into the cartridge slot 112 of the reader 100 as shown in FIG. 4, which illustrates the unlocked configuration of the reader 100. T reader door 110 is then closed over the cartridge 40, as shown FIGS. 5A and 5B, which illustrate the fixed/aligned configuration of the reader 100. In this configuration, (1) the cartridge 40 is fixed relative to the reader 100 such that the light source 125 and light detector 130 align in a fixed position with the first optical window 82; and (2) the biological sample piston 120 is aligned with the collection container 5 bottom. The user 25 is then prompted to confirm the test information and to begin the predetermined testing protocol on the reader 100. The protocol for testing is provided by the mobile application 4 that matches the kit scanned and provides the testing conditions to the reader 100.

After the cartridge 40 is docked with the reader 100, the biological sample piston 120 is actuated by the processor 175 to apply pressure on the tube bottom 22 forcing the biological sample 30 into the cartridge 40. The biological sample 30 may be incubated using heat and/or buffers prior to actuation of the piston. The heating element 160 is housed within the door 110 of the reader 100 (surrounding the collection container 5) and is controlled via the onboard processor 175, as are the buffer piston 165 that control the amount of buffer introduced into the biological sample 30. The sample is then filtered through a biomarker sorbent beads 60 or similar filter and can be washed and eluted specific to the validated test conditions.

The biological sample then migrates via valve 65 controlled by the reader 100 into to the multiple reaction chambers 80. After the biological sample 30 has filled each reaction chamber 80 (the number of chambers may vary by test type), the reaction chambers 80 will be heated by the heating elements (140, 145) on both sides of the cartridge 40. The heating elements (140, 145) have holes in them for the light source 125 and optional filters on one side, and for the light detector 130 and optional filters on the other side. Each reaction chamber 80 can be prepopulated with a single assay or with multiplexed biomarker assays. As the reaction chambers 80 are heated, the light detector 130 measurements will be taken throughout the reaction to measure either the accrual of amplification reagents or the absence thereof. Once the reader 100 determines that sufficient data has been collected to complete the test, the data collection will be stopped, and the results will then be finalized and available via the mobile application 4.

This system has many advantages and features over the prior art. For example, unlike current solutions that require multiple handling steps for the sample outside of the cartridge, the system integrates many of the key mechanical and control processes, resulting in a more simple and cost-effective process using single-use and target-specific cartridges. The single-use collection container 5 enables non or minimally invasive non-healthcare setting collection that integrates into the cartridge/reader, and enables the use of a multiple biological samples (saliva, swab, urine, etc) to be processed and prepared and directly input into the cartridge for analysis. The optical detection in the reader can analyze multiple bio marker applications (nucleic acids and proteins) at a multiplex level that allows for testing of broad diagnostic panels to cover a specific set of clinical symptoms. The optical detection also covers a broad range of existing detection methodologies such as fluorescence, colorimetric, and any other detection methodology using 400-800 nm optical windows for analyte detection to be modified and optimized for the non-healthcare setting.

The mobile application with cloud-based connectivity from the reader makes firmware updates, analysis software installation, and direct reporting of results to cloud possible. The cloud-based nature means that telemed PCPs can interface immediately with patients and provide e-prescriptions, which help patients avoid an in-person PCP visit.

Also, the panel based cartridges (respiratory, STI, UTI, etc.) described above use optical detection, versus lateral flow impedance in most, if not all, of the non-healthcare setting diagnostics competition. Optical detection will expand the capabilities of non-healthcare setting diagnostics. For example, multiplexing is highly desirable for end users as they do not have to guess what specific infection or problem they need testing for. A single cartridge can offer all the necessary tests, as opposed to the current state of the art that requires several different tests while attempting to identify the issue.

The system is designed to process both molecular (isothermal PCR and PCR) as well as ELISA cartridges, which provides an expansive potential product menu. ELISA targets antibodies and is generally used for protein detection (e.g. hormones, microbiology, blood screening, and immunology. Molecular is used for infections as well as viral and bacterial, but can also be used for human genetics for single nucleotide polymorphisms. Thus, any test that targets protein or nucleic acids can potentially be designed in a multiplex format to be used in the described system. The system can analyze both continuous assays and end-point assays. Analysis of both target biomarkers and controls can be performed in multiple ways due to the multisampling capabilities including threshold and standard curve.

Finally, no one is filling this market. Larger diagnostic companies are focused on lab, hospital and point-of-care devices. Many of these solutions are not currently suited for the non-healthcare setting diagnostic environment due to the process complexity and the requisite pricing.

Any of the suitable technologies, materials, and designs set forth and incorporated herein may be used to implement various example aspects of the invention, as would be apparent to one of skill in the art.

Although exemplary embodiments and applications of the invention have been described herein including as described above and shown in the included example Figures, there is no intention that the invention is limited to these exemplary embodiments and applications or to how the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system, or method falls within the scope of one of the claims that are allowed by the patent office based on this or any related patent application.

The invention claimed is:

1. A kit for diagnosing a biological sample from a user, the kit comprising:
a collection container comprising:
a collection tube with a tube bottom; and
a cap comprising a cap outlet;
wherein when the cap is arranged on the collection tube such that the collection tube and cap define a tube volume that holds the biological sample;
and wherein the tube bottom is constructed to slide within the collection tube, thereby changing the tube volume;
a cartridge comprising:
a container port constructed to removably dock with the collection container;
a reaction chamber with a first optical window that allows light to pass there through, the reaction chamber comprising one or more assays that each interacts with a target (1) interact with a target in the biological sample when the target is present, and (2) change a spectral characteristic of light directed into the reaction chamber when there is an interaction; and
a microfluidic channel fluidly connecting the container port to the reaction chamber;
a reader comprising:
a cartridge slot;
a light source;
a door with a sample injection piston;
a light detector;
a transmitter;
an unlocked configuration, wherein the cartridge may be installed into or uninstalled from the cartridge slot;
a fixed/aligned configuration, wherein the cartridge with a docked collection container is arranged into the cartridge slot, and the door is closed such that:
the cartridge is fixed relative to the reader and the light source;
light detector align in a fixed position with the first optical window; and
the sample injection piston aligns with the tube bottom;
a processor connected to the light source, the sample injection piston, the light detector, and the transmitter, the processor configured to perform the following steps in the fixed/aligned configuration:
actuate the sample injection piston to push the tube bottom, reducing the tube volume, thereby forcing the biological sample from the collection container, through the cap outlet, the container port, the microfluidic channel and to the reaction chamber;
actuate the light source;
receive data from the light detector; and
transmit to an external processor via the transmitter a result based on the data.

2. The kit of claim 1, wherein the target is a small molecule, protein, DNA, RNA, a virus or a bacterium.

3. The kit of claim 1, wherein:
the cartridge comprises multiple reaction chambers, each with an optical window that allows light to pass there through, the multiple reaction chambers fluidly connected to the container port via the microfluidic channel; and
the reader comprises:
multiple light sources that directs light through the optical windows of the multiple reaction chambers; and
multiple light detectors that detect the light within the multiple reaction chambers;

wherein the processor is connected to the multiple light sources and the multiple light detectors, and the wherein processors is configured to perform the following steps:
actuate the multiple light sources; and
receive data from the multiple light detectors.

4. The kit of claim 3, wherein the multiple reaction chambers each comprises one or more assays that (1) interacts with a target in the biological sample when the target is present, and (2) changes a spectral characteristic of the light directed into the reaction chamber when there is an interaction.

5. The kit of claim 4, wherein the target is a small molecule, protein, DNA, RNA, a virus or a bacterium.

6. The kit of claim 3, wherein:
the multiple reaction chambers comprises a first reaction chamber and a second reaction chamber;
the first reaction chamber comprises one or more assays that (1) interacts with a first target in the biological sample when the first target is present, and (2) changes a spectral characteristic of the light directed into the first reaction chamber when there is an interaction;
the second reaction chamber comprises one or more assays that (1) interacts with a second target in the biological sample when the second target is present, and (2) changes a spectral characteristic of the light directed into the second reaction chamber when there is an interaction; and
the first target is different than the second target.

7. The kit of claim 6, wherein the target is a protein, DNA, RNA, a virus or a bacterium.

8. The kit of claim 1, wherein the light source is an LED array or a laser.

9. The kit of claim 1, wherein the light detector is a photodiode array, a CCD sensor or a CMOS sensor.

10. The kit of claim 1, wherein the collection container comprises a buffer to preserve the biological sample.

11. The kit of claim 10, wherein the cap comprises the buffer, and the buffer is released into the biological sample when the cap is mounted onto the collection tube.

12. The kit of claim 1, wherein the tube bottom comprises a gasket that forms a seal against an interior wall of the collection tube.

13. The kit of claim 1, wherein the cartridge comprises an extraction buffer reservoir fluidly connected to the reaction chamber, the extraction buffer reservoir containing an extraction buffer.

14. The kit of claim 13, wherein the extraction buffer reservoir comprises a reservoir volume and a movable wall that varies the reservoir volume.

15. The kit of claim 14, wherein the reader futher comprises:
a buffer injection piston connected to the processor, wherein the buffer injection piston engages the movable wall;
wherein the processor actuates the buffer injection piston and pushes the moveable wall, reducing the reservoir volume, thereby forcing the extraction buffer into the reaction chamber.

16. The kit of claim 1, wherein the cartridge comprises a valve that regulates the flow of the biological sample between the container port and the reaction chamber.

17. The kit of claim 16, wherein the reader comprises a valve controller connected to the processor, the valve controller adapted to control the valve.

18. The test kit of claim 17, wherein the valve controller comprises a magnetic field to control the valve.

19. The kit of claim 1, wherein the cartridge comprises a waste chamber fluidly connected to the container port.

20. The kit of claim 19, wherein the cartridge comprises a valve that regulates the flow of the biological sample between the container port and the reaction chamber, and regulates the flow of the biological sample between the container port and the waste chamber.

21. The kit of claim 19, wherein the waste chamber comprising a vent.

22. The kit of claim 1, wherein the reaction chamber comprising a vent.

23. The kit of claim 1, wherein the reaction chamber has a second optical window opposite to the first optical window, and wherein the light detector is adjacent to the first optical window, while the light source is adjacent to the second optical window.

24. The kit of claim 1, wherein the microfluidic channel comprises a filter.

25. The kit of claim 1, wherein the microfluidic channel comprises one or more check valves.

26. The kit of claim 1, wherein the reader comprises a heating element connected to the processor.

27. The test kit of claim 26, wherein the heating element is positioned to heat the collection container.

28. The test kit of claim 26, wherein the heating element is positioned to heat the reaction chamber.

29. The test kit of claim 26, wherein:
the cartridge comprises a second reaction chamber;
the heating element is positioned to heat the reaction chamber and the second reaction chamber;
the heating element is configured to heat the reaction chamber to a first temperature and to heat the second reaction chamber to a second temperature; and
the first temperature is different from the second temperature.

30. The kit of claim 1, wherein the reader comprises two heating elements connected to the processor, one of which is positioned to heat the collection container, and the other of which is positioned to heat the reaction chamber.

31. The kit of claim 1, wherein the reader comprises a status indicator.

32. The kit of claim 1, wherein the reader comprises a temperature sensor connected to the processor.

33. The kit of claim 1, wherein the reader comprises a humidity sensor connected to the processor.

34. The kit of claim 1, wherein the cartridge slot comprises a clamp that mechanically constricts onto the cartridge.

35. The kit of claim 34, wherein the clamp is a spring-loaded mechanism.

36. The kit of claim 34, wherein the wherein the clamp is an electromechanical device connected to the processor, and wherein the processor actuates the electromechanical device.

* * * * *